US00PP29668P3

(12) United States Plant Patent
Harbage

(10) Patent No.: US PP29,668 P3
(45) Date of Patent: Sep. 11, 2018

(54) ***CANNA* PLANT NAMED 'LONGWOOD SIMPLY SALMON'**

(50) Latin Name: ***Canna* x *generalis***
Varietal Denomination: Longwood Simply Salmon

(71) Applicant: Longwood Gardens, Inc., Chester, PA (US)

(72) Inventor: James F. Harbage, Atglen, PA (US)

(73) Assignee: Longwood Gardens, Inc., Chester, PA (US)

( * ) Notice: Subject to any disclaimer, the term of this patent is extended or adjusted under 35 U.S.C. 154(b) by 28 days.

(21) Appl. No.: 15/330,690

(22) Filed: Oct. 27, 2016

(65) Prior Publication Data

US 2018/0124988 P1 May 3, 2018

(51) Int. Cl.
*A01H 5/02* (2018.01)
*A01H 6/56* (2018.01)

(52) U.S. Cl.
USPC ..... Plt./415
CPC ..... *A01H 5/02* (2013.01); *A01H 5/0272* (2013.01); *A01H 6/56* (2018.05)

(58) Field of Classification Search
USPC ..... Plt./415
See application file for complete search history.

*Primary Examiner* — Keith O. Robinson
(74) *Attorney, Agent, or Firm* — Barbara Campbell; Cochran Freund & Young LLC

(57) ABSTRACT

A new and distinct cultivar of *Canna* plant named 'Longwood Simply Salmon' characterized by dwarf habit, gray-green foliage, and orange-salmon flowers which are open faced, long-lived, and attractively arranged within the inflorescence, is disclosed.

2 Drawing Sheets

Figure 1:
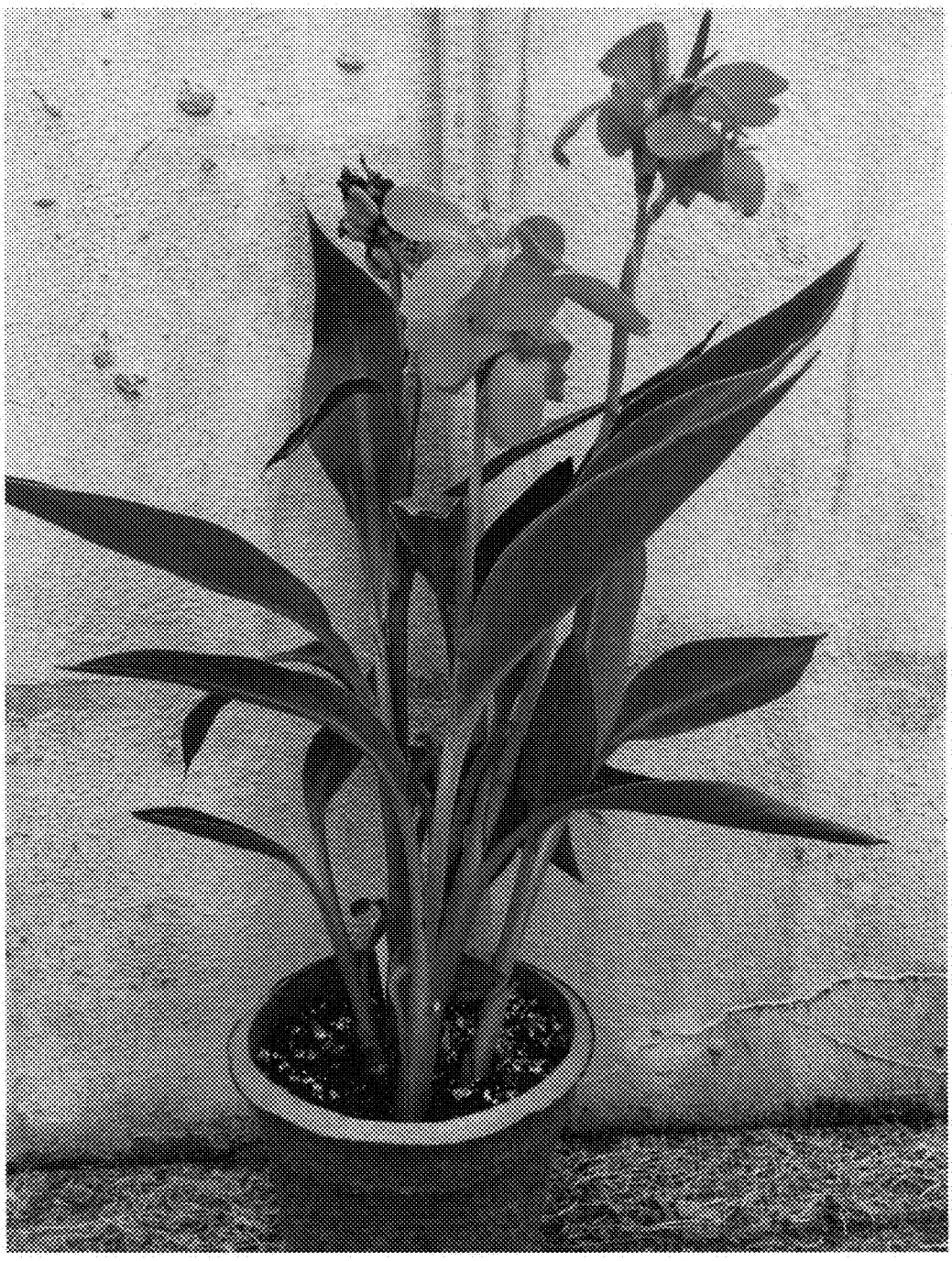

Genus and species: *Canna* x *generalis*.
Variety denomination: 'Longwood Simply Salmon'.

BACKGROUND OF THE NEW PLANT

The present invention relates to a new and distinct cultivar of *Canna*, also known as *Canna* Lily or Indian Shot, which is grown as an ornamental annual or perennial, according to climate zone, for use in planted containers and in the garden and landscape. The new cultivar is known botanically as *Canna* x *generalis*, and will be referred to hereinafter by the cultivar name 'Longwood Simply Salmon'.

A *Canna* breeding program has been carried out at Longwood Gardens in Kennett Square, Pa. since 1967. The aim of the breeding program is to develop new dwarf or semi-dwarf *canna* varieties in various flower colors and foliage colors, with well-formed inflorescences consisting of flowers which are self-cleaning.

'Longwood Simply Salmon' arose and was selected in 2009 as an open-pollinated seedling which had been grown from seed collected from open pollination of *Canna* 2008-0552 (code number, unreleased, unpatented) which is part of the breeding stock from the historic breeding program at Longwood Gardens. The open-pollination occurred on the inventor's property in Kennett Square, Pa.

'Longwood Simply Salmon' was first asexually reproduced at Longwood Gardens in 2009. Asexual propagation was accomplished by division of the rhizome. Since that time, under careful observation, the distinguishing characteristics of 'Longwood Simply Salmon' have been determined stable and uniform, and to reproduce true to type in successive generations of asexual propagation via division of the rhizome. In 2010, 'Longwood Simply Salmon' was established in tissue culture and has been reproduced true to type by this means, in addition to reproduction by means of division.

SUMMARY

The distinguishing characteristics of 'Longwood Simply Salmon' are as follows. 'Longwood Simply Salmon' was has not been tested under all possible conditions and phenotypic differences may be observed with variations in environmental, climatic, and cultural conditions.

1. 'Longwood Simply Salmon' is dwarf, achieving a height 55 cm to 69 cm (including the inflorescence) in one year of growth in a 2 gallon container.
2. 'Longwood Simply Salmon' exhibits early basal branching, giving rise to a fuller display in containers and in the landscape.
3. The foliage of 'Longwood Simply Salmon' is gray-green in color.
4. The inflorescence of 'Longwood Simply Salmon' is salmon-orange in color.
5. Each flower (actually, staminode cluster) of 'Longwood Simply Salmon' is long-lived, remaining attached to the inflorescence for 7 to 10 days.
6. The old flowers of 'Longwood Simply Salmon' fall away from the inflorescence without lodging within, that is, the flowers are self-cleaning.
7. The inflorescence of 'Longwood Simply Salmon' becomes large and showy, consisting of 4 to 7 open flowers before the oldest flower falls away.
8. The flowers of 'Longwood Simply Salmon' are open faced and attractively arranged within the inflorescence.

DESCRIPTION OF THE PHOTOGRAPHS

The accompanying color photographs illustrate the overall appearance of 'Longwood Simply Salmon' showing the color of the inflorescence and the foliage as true as it is reasonably possible to obtain in colored reproductions of this type. All photographs were taken in August 2016.

FIG. 1 depicts a 5-month old plant of 'Longwood Simply Salmon' which has been grown in a 6 inch container in a greenhouse in Kennett Square, Pa. The plant has been grown without any chemical growth retardant. This photograph shows the early basal branching of 'Longwood Simply Salmon'.

Figure 2:
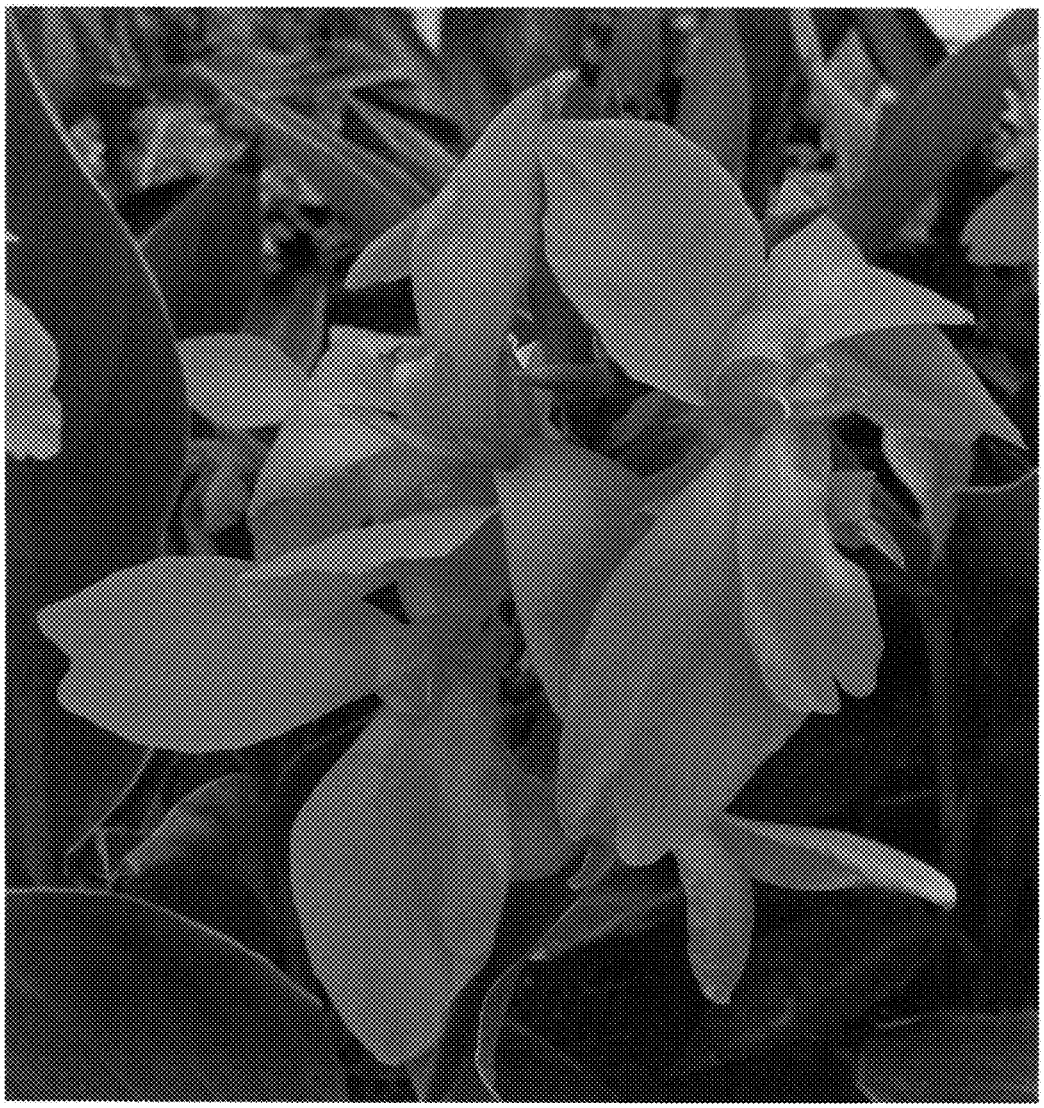

FIG. 2 depicts a close-up view of the inflorescence of 'Longwood Simply Salmon'. In this photograph, 7 flowers (actually staminodes) are fully developed with approximately 11 further buds in various stages of development.

DESCRIPTION OF THE NEW VARIETY

In the following botanical description, all color references are made to The Royal Horticultural Society Colour Chart, 2015 Edition, except where general terms of ordinary dictionary significance are used.

The plant used for this botanical description was 5-months old from a tissue cultured division and had been grown in a 1-gallon container under greenhouse conditions is Kennett Square, Pa. Botanical descriptions were taken in August 2016.

Botanical classification:

*Genus and species.*—*Canna* x *generalis.*

Parentage: From open pollination of *Canna*, code number *Canna* 2008-0552.

Plant:

*Propagation.*—By division of rhizomes or division of tissue cultured plants.

*Cultural suggestions.*—In common with *Cannas* generally, 'Longwood Simply Salmon' is evergreen in warm climates, but will die back as winter approaches in cool climates. Rhizomes may be mulched to protect from light frost but should be lifted and stored if the ground is liable to freeze below the surface.

*Hardiness.*—'Longwood Simply Salmon' is hardy and evergreen in USDA Zone 8.

*Heat tolerance.*—Plants grow and flower rapidly in sunny positions.

*Pest and disease resistance or susceptibility.*—'Longwood Simply Salmon' has not been found to be more or less resistant or susceptible to the pests and diseases which affect the genus and its cultivars, of which *Canna* yellow streak virus (synonym bean yellow mosaic virus, genus *Potyvirus* and *Canna* yellow mottle virus (synonym *Canna* yellow mosaic virus, genus *Badnavirus*) are endemic in many *Canna* plants in the landscape.

*Plant form.*—Upright with one or more basal branch shoots.

*Rhizome description.*—Thick, fibrous, 1.4 cm to 1.5 cm in diameter, with papery scales which are white 166C in color when first forming, becoming moderate brown 200C as they age and peel away from the rhizome whose revealed surface is smooth, cream NN155C.

*Plant height after one year in a 2-gallon container.*—55 cm to 69 cm (including inflorescence).

*Plant spread.*—44 cm to 64 cm.

Stem (each basal shoot, to base of inflorescence):

*Length.*—43 cm to 56 cm.

*Diameter.*—2.3 cm.

*Internode length.*—6.1 cm to 12.3 cm.

*Stem strength.*—The stem is firm and fleshy towards base, becoming very hard and stiff towards the inflorescence.

*Texture.*—Slightly rough with longitudinal ribs towards base, smooth towards inflorescence.

*Color.*—139C at the base, 139D above the highest leaf.

Foliage:

*Form.*—Simple and entire.

*Leaf arrangement.*—Alternate.

*Leaf length.*—20 cm to 31 cm.

*Leaf width.*—6 cm to 13 cm.

*Shape.*—Ovate.

*Apex.*—Acute.

*Base.*—Obtuse.

*Margin.*—Entire.

*Surface texture* (*both surface*).—Glabrous.

*Leaf structure.*—Leaf is supported by a stiff depressed midrib and by raised parallel lateral ribs which are spaced approximately 1 cm apart.

*Venation.*—Pinnate.

*Vein color* (*both surfaces*).—140D.

*Leaf color* (*both surfaces*).—139A towards the apex, and N138C towards the base.

*Petioles.*—Arrangement: Sheathing. Length: 3 cm to 9.4 cm. Texture: Glabrous, ribbed. Color, upper surface: 141D. Color, lower surface: 144B becoming 143C where petiole is exposed to full sun.

Inflorescence:

*Form.*—Terminal raceme consisting of 10 to 19 flowers.

*Height* (*fully developed*).—12 cm to 20 cm.

*Diameter* (*fully developed*).—14 cm.

*Bract.*—Raceme is subtended by single paper-like bract.

*Bract shape.*—Cymbiform.

*Peduncle.*—Dimensions: 11 cm to 19 cm in length, 0.4 cm in diameter. Strength: Hard and very stiff. Texture: Glabrous. Color: 142B.

Flower:

*Overall description.*—Flower is complex, comprised of three short waxy sepals and three narrow petals. The showy elements of the flower are modified petaloid stamens or staminodes of which three outer staminodes are large and wide, and a fourth is narrow and recurving (labellum). A fifth (inner) staminode bears a lone marginal anther and is adjacent to a long slender petaloid style.

*Natural flowering season.*—Continually from late spring until fall.

*Flower longevity on the plant.*—7 to 10 days.

*Flower fragrance.*—None.

*Flower dimensions.*—13.2 cm in height, 6.8 cm to 8.4 cm in width.

*Pedicels.*—Dimensions: 0.4 cm in length, 0.3 cm in diameter. Texture: Glabrous. Color: 143B.

*Buds.*—Dimensions: 5.1 cm to 5.5 cm in length, 0.6 c to 0.7 cm in width. Shape: Ellipsoid. Surface texture: Smooth, appears slightly farinaceous. Color: 42A.

*Sepals.*—Number: 3, fused at base. Dimensions: 8 mm in length, 4 mm in width. Shape: Elliptic, apex acute, base truncate. Color: Adaxial surface 142B, abaxial surface 142B. Surface texture (both surfaces): Farinaceous, waxy.

*Petals*.—Number: 3, fused at base. Dimensions: 3.3 cm to 4.5 cm in length, 1 mm in width. Shape: Elongate elliptic, apex acute, base truncate. Margin: Smooth, entire. Color (both surfaces): Adaxial surface 24B, abaxial surface 34A. Surface texture (both surfaces): Glabrous.

*Outer staminodes*.—Number: 3, fused at base. Arrangement: Moderately overlapping. Shape, dimensions: staminodes broad obovate, apex round, base truncate, 8.5 cm in length, 3.6 cm in width; staminode (labellum) spatulate, recurving, 6.8 cm in length, 2.2 cm in width. Reflexing: The distal third of each outer staminode is weakly reflexed. Margin: Smooth, entire, undulating. Color (both surfaces): Adaxial surface 33B, abaxial surface 33A. Surface texture (both surfaces): Glabrous.

*Inner staminode* (*anther bearing*).—Arrangement: Nested among, and moderately overlapping the staminodes. Shape: Spatulate, apex round, base truncate. Dimensions: 5.9 cm to 6.6 cm in length, 0.7 cm to 0.8 cm in width. Reflexing: The distal half of the inner staminode is weakly to moderately reflexed. Margin: Smooth, entire. Color (both surfaces): Adaxial surface 33B, abaxial surface 33B. Surface texture (both surfaces): Glabrous.

*Inner petaloid style*.—Shape: Falcate, apex truncate, base truncate. Dimensions: 4.8 cm in length, 4 mm in width. Margin: Smooth, entire. Color (both surfaces): Adaxial surface 14A, abaxial surface 14A. Surface texture (both surfaces): Glabrous.

Reproductive organs:

*Stamens*.—Petaloid anther-bearing staminode as above.

*Anthers*.—Not always present; where present, fused along half anther length to concave margin of staminode.

*Anther shape*.—Rectangular.

*Anther dimensions*.—Length 5 mm, width 1 mm.

*Color*.—12D.

*Pollen amount*.—Slight, appears to transfer to style before flower opens.

*Pollen color*.—12D.

*Style, stigma*.—1 petaloid style as above; stigma absent.

*Ovary*.—Inferior, 3-carpellate, surface rough with many tiny pinhead-like protrusions, color 142A.

Seed: Seed has not been observed.

COMPARISON TO PARENTAL VARIETY AND COMMERCIAL VARIETY

The male parent of 'Longwood Simply Salmon' is unknown. The female parent, *Canna* '2008-0552', may be compared to 'Longwood Simply Salmon' by flower color. Whereas the flowers of 'Longwood Simply Salmon' are salmon-orange in color, the flowers of '2008-0552' are pink in color. The variety of *Canna* which is considered by the inventor to most closely resemble 'Longwood Simply Salmon' is *Canna* 'Tropical Salmon' (seed-raised, unpatented). Whereas 'Tropical Salmon' is a seed-raised variety, 'Longwood Simply Salmon' is reproduced asexually by division or tissue culture. Although the flowers of both varieties are salmon-orange in color, the flowers of 'Tropical Salmon' are deeper in color whereas the flowers of 'Longwood Simply Salmon' are soft salmon in color. In addition, the leaves of 'Tropical Salmon' are broad and mid-green in color, whereas the leaves of 'Longwood Simply Salmon' are longer and narrower, and gray-green in color.

I claim:

1. A new and distinct variety of *Canna* plant named 'Longwood Simply Salmon' as shown and described herein.

* * * * *